(12) United States Patent
Dietz

(10) Patent No.: US 10,234,458 B2
(45) Date of Patent: Mar. 19, 2019

(54) METHODS AND MATERIALS FOR TREATING RENAL CELL CARCINOMA

(71) Applicant: Mayo Foundation for Medical Education and Research, Rochester, MN (US)

(72) Inventor: Allan B. Dietz, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/643,155

(22) Filed: Jul. 6, 2017

(65) Prior Publication Data
US 2017/0307617 A1    Oct. 26, 2017

Related U.S. Application Data

(63) Continuation of application No. 14/994,980, filed on Jan. 13, 2016, now Pat. No. 9,733,248, which is a continuation of application No. 13/509,089, filed as application No. PCT/US2010/055856 on Nov. 8, 2010, now Pat. No. 9,266,957.

(60) Provisional application No. 61/259,879, filed on Nov. 10, 2009.

(51) Int. Cl.
| | |
|---|---|
| *A61N 5/10* | (2006.01) |
| *A61K 39/00* | (2006.01) |
| *C07K 16/22* | (2006.01) |
| *C07K 16/28* | (2006.01) |
| *G01N 33/574* | (2006.01) |

(52) U.S. Cl.
CPC ......... *G01N 33/57407* (2013.01); *A61N 5/10* (2013.01); *C07K 16/22* (2013.01); *C07K 16/2896* (2013.01); *G01N 33/57438* (2013.01); *A61K 2039/505* (2013.01); *G01N 2333/70503* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,376,202 B1 | 4/2002 | Davis |
| 9,266,957 B2 | 2/2016 | Dietz |
| 2007/0031443 A1 | 2/2007 | Vaishnaw et al. |
| 2008/0057043 A1 | 3/2008 | Naldini et al. |
| 2012/0141514 A1 | 6/2012 | Kuehne et al. |
| 2012/0183575 A1 | 7/2012 | Gabrielsson |
| 2012/0230989 A1 | 9/2012 | Dietz |
| 2012/0276004 A1 | 11/2012 | Epstein et al. |

FOREIGN PATENT DOCUMENTS

WO    WO2012138857    10/2012

OTHER PUBLICATIONS

Appay et al., "Immuno-monitoring of CD8+ T cells in whole blood versus PBMC samples," *J. Immunol. Methods.*, 309(1-2):192-199, Feb. 2006.
Asadullah et al., "Immunodepression following neurosurgical procedures," *Crit Care Med.*, 23(12):1976-1983, Dec. 1995.
Asadullah et al., "Very low monocytic HLA-DR expression indicates high risk of infection—immunomonitoring for patients after neurosurgery and patients during high dose steroid therapy," *Eur J Emerg Med.*, 2(4):184-190, Dec. 1995.
Atzpodien et al., "Adjuvant treatment with interleukin-2- and interferon-alpha2a-based chemoimmunotherapy in renal cell carcinoma post tumour nephrectomy: results of a prospectively randomised trial of the German Cooperative Renal Carcinoma Chemoimmunotherapy Group (DGCIN)," *Br J Cancer.*, 92(5):843-846, Mar. 14, 2005.
Autissier et al., "Evaluation of a 12-color flow cytometry panel to study lymphocyte, monocyte, and dendritic cell subsets in humans," *Cytometry A.*, 77(5):410-419, May 2010.
Axtelle and Pribble, "IC14, a CD14 specific monoclonal antibody, is a potential treatment for patients with severe sepsis," *J Endotoxin Res.*, 7(4):310-314, 2001.
Barham, "Cell-surface IL-7 receptor expression facilitates the purification of FOXP3(+) regulatory T cells," *Trends Immunol.*, 27(12):541-544, Epub Oct. 12, 2006.
Bauer et al., "Accuracy of waste blood measurement in critically ill patients," *Intensive Care Med.*, 37(4):721-722, Epub Jan. 18, 2011.
Bernard et al., "Report of the American-European consensus conference on ARDS: definitions, mechanisms, relevant outcomes and clinical trial coordination. The Consensus Committee," *Intensive Care Med.*, 20(3):225-232, 1994.
Bernard et al., "The American-European Consensus Conference on ARDS. Definitions, mechanisms, relevant outcomes, and clinical trial coordination," *Am. J. Crit. Care Med.*, 149(3):818-824, Mar. 1994.
Cheville et al., "Comparisons of outcome and prognostic features among histologic subtypes of renal cell carcinoma," *Am. J. Surg. Pathol.*, 27(5):612-624, May 2003.
Chow et al., "Rising incidence of renal cell cancer in the United States," *JAMA*, 281(17):1628-1631, May 1999.
Contal and O'Quigley, "An application of changepoint methods in studying the effect of age on survival in breast cancer," *Comput Stat Data Analysis.*, 30(3):253-270, May 28, 1999.
Davis, "A prescription for human immunology," *Immunity*, 29(6):835-838, Dec. 19, 2008.
de Jager et al., "Prerequisites for cytokine measurements in clinical trials with multiplex immunoassays," *BMC Immunol.*, 10:52, Sep. 28, 2009.

(Continued)

Primary Examiner — Karen A. Canella
(74) Attorney, Agent, or Firm — Fish & Richardson P.C.

(57) ABSTRACT

This document provides methods and materials related to treating renal cell carcinoma. For example, methods and materials for assessing a cancer patient (e.g., a renal cell carcinoma patient) for tumor or peritumoral tissue containing $CD14^+$ cells and proceeding with a cancer treatment option (e.g., a renal cell carcinoma treatment option) based on the presence, absence, or level of $CD14^+$ cells present within the tumor or peritumoral tissue are provided.

1 Claim, 4 Drawing Sheets

(56) References Cited

OTHER PUBLICATIONS

Deininger et al., "Expression and release of CD14 in astrocytic brain tumors," *Acta Neuropathol.*, 106(3):271-277, Epub Jun. 27, 2003.
Diaz-Montero et al., "Increased circulating myeloid-derived suppressor cells correlate with clinical cancer stage, metastatic tumor burden, and doxorubicin-cyclophosphamide chemotherapy," *Cancer Immunol Immunother.*, 58(1):49-59, print Jan. 2009, Epub Apr. 2008.
Ege et al., "Prediction of survival using absolute lymphocyte count for newly diagnosed patients with multiple myeloma: a retrospective study," *Br J Haematol*, 141(6):792-798, Jun. 2008.
Filipazzi et al., "Identification of a new subset of myeloid suppressor cells in peripheral blood of melanoma patients with modulation by a granulocyte-macrophage colony-stimulation factor-based anti-tumor vaccine," *J Clin Oncol.*, 25(18):2546-2553, Jun. 2007.
Gabrilovich and Nagaraj, "Myeloid-derived suppressor cells as regulators of the immune system," *Nat Rev Immunol.*, 9(3):162-174, Mar. 2009.
Gettman et al., "Pathologic staging of renal cell carcinoma: significance of tumor classification with the 1997 TNM staging system," *Cancer*, 91:354-361, Jan. 2001.
Gustafson et al., "Association of an increased frequency of CD14+ HLA-DR lo/neg monocytes with decreased time to progression in chronic lymphocytic leukaemia (CLL)," *Br J Haematol.*, 156(5):674-676, Epub Nov. 3, 2011.
Gustafson et al., "Immune monitoring using the predictive power of immune profiles," *J Immunother Cancer.*, 1:7, Jun. 27, 2013.
Gustafson et al., "Systemic immune suppression in glioblastoma: the interplay between CD14+HLA-DRlo/neg monocytes, tumor factors, and dexamethasone," *Neuro Oncol.*, 12(7):631-644, Epub Feb. 23, 2010.
Harton and Ting, "Class Ii transactivator: mastering the art of major histocompatibility complex expression," *Mol Cell Biol.*, 20(17):6185-6194, Sep. 2000.
Hoechst et al., "A new population of myeloid-derived suppressor cells in hepatocellular carcinoma patients induces CD4(+)CD25(+)Foxp3(+) T cells," *Gastroenterology*, 135(1):234-243, print Jul. 2008 Epub Mar. 2008.
Höflich et al., "Regulatory immunodeficiency and monocyte deactivation Assessment based on HLA-DR expression," *Clinical and Applied Immunology Reviews*, 2(6):337-344, Oct.-Dec. 2002.
International Preliminary Report on Patentability for Application No. PCT/US2011/058981, dated May 7, 2013, 4 pages.
International Preliminary Report on Patentability for PCT/US2010/055856, dated May 15, 2012, 5 pages.
International Preliminary Report on Patentability for PCT/US2013/069573, dated May 28, 2015, 13 pages.
International Preliminary Report on Patentability for PCT/US2014/037058, dated Nov. 19, 2015, 6 pages.
International Search Report and Written Opinion for Application No. PCT/US2011/058981, dated Apr. 27, 2012, 5 pages.
International Search Report and Written Opinion for PCT/US2010/055856, dated Aug. 1, 2011, 6 pages.
International Search Report and Written Opinion for PCT/US2013/069573, dated Feb. 27, 2014, 9 pages.
International Search Report and Written Opinion for PCT/US2014/37058, dated Sep. 29, 2014, 7 pages.
Iscimen et al., Risk factors for the development of acute lung injury in patients with septic shock: an observational cohort study, *Crit Care Med.*, 36(5):1518-1522, May 2008.
Iwakami et al., "Granulocyte and monocyte adsorption apheresis therapy modulates monocyte-derived dendritic cell function in patients with ulcerative colitis," *Ther Apher Dial.*, 13(2):138-146, Apr. 2009.
Kiertscher et al., "Tumors promote altered maturation and early apoptosis of monocyte-derived dendritic cells," *J Immunol.*, 164(3):1269-1276, Feb. 2000.
Ko et al., "Sunitinib mediates reversal of myeloid-derived suppressor cell accumulation in renal cell carcinoma patients," *Clin Cancer Res.*, 15(6):2148-2157, Epub Mar. 10, 2009.

Kohrt et al., "Profile of immune cells in axillary lymph nodes predicts disease-free survival in breast cancer," *PLoS Med.*, 2(9):e284, Epub Sep. 6, 2005.
Lin et al., "Immunosuppressive CD14+HLA-DR(low)/-monocytes in B-cell non-Hodgkin lymphoma," *Blood* 117(3):872-881, Jan. 20, 2011, Epub Nov. 9, 2010.
Longo et al., "Single-cell network profiling of peripheral blood mononuclear cells from healthy donors reveals age- and race-associated differences in immune signaling pathway activation," *J Immunol.*, 188(4):1717-1725, Epub. Jan. 13, 2012.
Maas et al., "Immune profiles of pediatric cancer patients," presented at the Society for Immunotherapy of Cancer 2011 Annual Meeting, Nov. 4-6, 2011, 1 page.
Mayo Clinic, ClinicalTrials.gov Identifier: NCT00562328, "Rituximab, Alemtuzumab, and GM-CSF as First-Line Therapy in Treating Patients With Early-Stage Chronic Lymphocytic Leukemia," ClinicalTrials.gov [online] Nov. 21, 2007 [retrieved Oct. 28, 2015]. Retrieved from the Internet: <URL: https://www.clinicaltrials.gov/ct2/show/NCT00562328?term=NCT00562328&rank=1>, 5 pages.
Minniti et al., "Phase II study of short-course radiotherapy plus concomitant and adjuvant temozolomide in elderly patients with glioblastoma," *Int J Radiat Oncol Biol Phys.*, 83(1):93-99, Epub Nov. 11, 2011.
Moore et al., "Postinjury multiple organ failure: a bimodal phenomenon," *J Trauma.*, 40(4):501-510; discussion 510-512, Apr. 1996.
Morimura et al., "Monocyte subpopulations in human gliomas: expression of Fc and complement receptors and correlation with tumor proliferation," *Acta Neuropathol.*, 80(3):287-294, 1990.
Ostrand-Rosenberg and Sinha, "Myeloid-derived suppressor cells. linking inflammation and cancer," *J Immunol.*, 182(8):4499-506, Apr. 2009.
Palmer et al., "Cell-type specific gene expression profiles of leukocytes in human peripheral blood," *BMC Genomics*, 7:115, May 16, 2006.
Peters et al., "Acquired immunoparalysis in paediatric intensive care: prospective observational study," *BMJ.*, 319(7210):609-610, Sep. 1999.
Porrata et al., "Early lymphocyte recovery predicts superior survival after autologous stem cell transplantation in non-Hodgkin lymphoma: a prospective study," *Biology of Blood & Marrow Transplantation*, 14(7):807-816, Jul. 2008.
Rapp et al., "Cellular immunity of patients with malignant glioma: prerequisites for dendritic cell vaccination immunotherapy," *J Neurosurg.*, 105(1):41-50, Jul. 2006.
Rittirsch et al., "Harmful molecular mechanisms in sepsis," *Nat Rev Immunol.*, 8(10):776-787, Oct. 2008.
Schimke et al., "Anti-CD14 mAb treatment provides therapeutic benefit after in vivo exposure to endotoxin," *Proc Natl Acad Sci U S A.*, 95(23):13875-13880, Nov. 1998.
Serafini et al., "Myeloid-derived suppressor cells promote cross-tolerance in B-cell lymphoma by expanding regulatory T cells," *Cancer Res.*, 68(13):5439-5449, Jul. 2008.
Serafini et al., "Phosphodiesterase-5 inhibition augments endogenous antitumor immunity by reducing myeloid-derived suppressor cell function," *J Exp Med.*, 203(12):2691-2702, Nov. 2006.
Sester et al., "Strong depletion of CD14(+)CD16(+) monocytes during haemodialysis treatment," *Nephrol Dial Transplant.*, 16(7):1402-1408, Jul. 2001.
Sinha et al., "Proinflammatory S100 proteins regulate the accumulation of myeloid-derived suppressor cells," *J Immunol.*, 181(7):4666-4675, Oct. 2008.
Soini et al., "Treatment of follicular non-Hodgkin's lymphoma with or without rituximab: cost-effectiveness and value of information based on a 5-year follow-up," *Ann Oncol.*, 22(5):1189-1197, Epub Dec. 6, 2010.
Takeda et al., "MHC class II molecules are not required for survival of newly generated CD4+ T cells, but affect their long-term life span," *Immunity*, 5(3):217-228, Sep. 1996.
Tokunaga et al., "Successful treatment of renal cell carcinoma with mediastinal lymph node metastasis by interleukin-2: a case report," *Tokai J Exp Clin Med.*, 30(2):111-115, Jul. 2005.

(56) References Cited

OTHER PUBLICATIONS van Ravenswaay Claasen, "Tumor infiltrating cells in human cancer. On the possible role of CD16+ macrophages in antitumor cytotoxicity," *Lab Invest.*, 67(2):166-174, Aug. 1992.

Viret and Janeway, "MHC and T cell development," *Rev Immunogenet.*, 1(1):91-104, 1999.

Vuk-Pavlovic et al., "Rebuilding immunity in cancer patients," *Blood Cells Mol Dis.*, 40(1):94-100, print Jan-Feb 2008, Epub Sep. 2007.

Webster et al., "Mononuclear cell infiltration in clear-cell renal cell carcinoma independently predicts patient survival," *Cancer*, 107(1):46-53, Jul. 1, 2006.

Xin et al., "Sunitinib inhibition of Stat3 induces renal cell carcinoma tumor cell apoptosis and reduces immunosuppressive cells," *Cancer Res.*, 69(6):2506-2513, print Mar. 2009, Epub Feb. 2009.

Yu et al., [a study on HLA-Dr expression of brain tumor cells and mononuclear cell subsets infiltrating in these tumors], [Article in Chinese], Zhonghua Bing Li Xue Za Zhi, 23(4):221-223, Aug 1994, [English abstract only].

Zea et al., "Arginase-producing myeloid suppressor cells in renal cell carcinoma patients: a mechanism of tumor evasion," *Cancer Res.*, 65(8):3044-3048, Apr. 2005.

ns for Pat. No. 14/994,980,
METHODS AND MATERIALS FOR TREATING RENAL CELL CARCINOMA

CROSS REFERENCE TO RELATED APPLICATIONS

This application is a continuation of U.S. application Ser. No. 14/994,980, filed Jan. 13, 2016 (now U.S. Pat. No. 9,733,248), which is a continuation of U.S. patent application Ser. No. 13/509,089, filed May 10, 2012 (now U.S. Pat. No. 9,266,957), which is a National Stage application under 35 U.S.C. § 371 of International Application No. PCT/US2010/055856, having an International filing date of Nov. 8, 2010, which claims the benefit of U.S. Provisional Application Ser. No. 61/259,879, filed Nov. 10, 2009. The disclosures of the prior applications are considered part of (and are incorporated by reference in) the disclosure of this application.

BACKGROUND

1. Technical Field

This document relates to methods and materials involved in treating renal cell carcinoma. For example, this document provides methods and materials for assessing a renal cell carcinoma patient for tumor or peritumoral tissue containing CD14$^+$ cells and proceeding with a renal cell carcinoma treatment option based on the presence, absence, or level of CD14$^+$ cells present within the tumor or peritumoral tissue.

2. Background Information

The incidence and deaths caused by renal cell carcinoma are increasing in the United States. Of particular note, incidence and mortality rates for renal cell carcinoma have risen among both genders, and these trends are not explained by the increased use of abdominal imaging (Chow et al., *JAMA*, 281:1628-31 (1999)). Indeed, mortality from renal cell carcinoma has increased over 30% since 1950. One treatment for renal cell carcinoma is surgical resection. The majority of patients with renal cell carcinoma confined to the kidney can be cured by surgery; however, about 30 percent of patients can develop metastases and require additional treatments.

Renal cell carcinoma encompasses a group of at least five subtypes with unique morphologic, genetic, and behavioral characteristics (Cheville et al., *Am. J. Surg. Pathol.*, 27:612-24 (2003)). Cancer-specific survival is dependent on subtype, and over 80 percent of renal cell carcinomas and the vast majority of renal cell carcinoma-related deaths are due to clear cell renal cell carcinoma. To date, tumor stage and grade are the primary prognostic indicators for patients with clear cell renal cell carcinoma treated by nephrectomy (Gettman et al., *Cancer*, 91:354-61 (2001)). There is, however, variability in patient outcome that cannot be explained by the combination of stage and grade.

SUMMARY

This document relates to methods and materials involved in treating renal cell carcinoma. For example, this document provides methods and materials for assessing a renal cell carcinoma patient for tumor or peritumoral tissue containing CD14$^+$ cells and proceeding with a renal cell carcinoma treatment option based on the presence, absence, or level of CD14$^+$ cells present within the tumor or peritumoral tissue.

As described herein, the presence of a moderate to marked level of CD14$^+$ cells within tumor or peritumoral tissue of a renal cell carcinoma patient can indicate that it is unlikely that the renal cell carcinoma patient will respond positively to a standard renal cell carcinoma treatment that is appropriate for renal cell carcinoma patients lacking a moderate to marked level of CD14$^+$ cells within their tumor and peritumoral tissue. A standard renal cell carcinoma treatment that is appropriate for renal cell carcinoma patients lacking a moderate to marked level of CD14$^+$ cells within their tumor and peritumoral tissue can be referred to as a type A treatment. The presence of a moderate to marked level of CD14$^+$ cells within tumor or peritumoral tissue of a renal cell carcinoma patient also can indicate that it is likely that the renal cell carcinoma patient will respond positively to a renal cell carcinoma treatment that is appropriate for renal cell carcinoma patients having a moderate to marked level of CD14$^+$ cells within their tumor and peritumoral tissue. A renal cell carcinoma treatment that is appropriate for renal cell carcinoma patients having a moderate to marked level of CD14$^+$ cells within their tumor and peritumoral tissue can be referred to as a type B treatment. As also described herein, the absence of a moderate to marked level of CD14$^+$ cells within tumor or peritumoral tissue of a renal cell carcinoma patient can indicate that it is likely that the renal cell carcinoma patient will respond to a type A treatment and/or that it is not necessary to proceed with a type B treatment.

The methods and materials provided herein can allow clinicians to determine proper treatment options for cancer patients (e.g., renal cell carcinoma patients). For example, the methods and materials provided herein can be used to identify renal cell carcinoma patients who would benefit from a type A treatment or a type B treatment. In some cases, the methods and materials provided herein can be used to identify renal cell carcinoma patients who would benefit from switching from a type A treatment to a type B treatment. Identifying cancer patients who would benefit from a particular treatment option can avoid unnecessary treatment attempts and unnecessary patient suffering.

In general, one aspect of this document features a method for treating a human having renal cell carcinoma. The method comprises, or consists essentially of, (a) determining whether or not tumor or peritumoral tissue from the human contains greater than 30 percent of CD14$^+$ cells, and (b) proceeding with a type B treatment if the tissue contains greater than 30 percent of CD14$^+$ cells, and proceeding with a type A or type B treatment if the tissue does not contain greater than 30 percent of CD14$^+$ cells. The renal cell carcinoma can be clear cell renal cell carcinoma. The step (a) can comprise determining whether or not the tumor tissue contains greater than 30 percent of CD14$^+$ cells. The step (a) can comprise determining whether or not the peritumoral tissue contains greater than 30 percent of CD14$^+$ cells. The step (a) can comprise determining whether or not the tumor or peritumoral tissue contains greater than 35 percent of CD14$^+$ cells. The step (a) can comprise determining whether or not the tumor or peritumoral tissue contains greater than 40 percent of CD14$^+$ cells. The step (a) can comprise determining whether or not the tumor or peritumoral tissue contains greater than 30 percent of CD14$^+$ cells in a diffuse staining pattern. The tumor or peritumoral tissue from the human can contain greater than 30 percent of CD14$^+$ cells. The method can comprise proceeding with a type B treatment selected from the group consisting of chemotherapies, biologic therapies, and cell therapies. The method can comprise proceeding with a type B treatment selected from the group consisting of treatment with Sunitinib, treatment with Sorafenib, treatment with Bevacizumab, treatment with Temsirolimus, and treatment with Everolimus. The method can comprise initiating a type B treatment for the human after the step (a). The tumor or peritumoral tissue from the human can lack greater than 30 percent of CD14$^+$ cells. The method can comprise performing a surgical treatment after the step (a).

In another aspect, this document features a method for treating a human having renal cell carcinoma. The method comprises, or consists essentially of, (a) determining whether or not tumor or peritumoral tissue from the human contains greater than 10 percent of CD14$^+$ cells, and (b) proceeding with a type B treatment if the tissue contains greater than 10 percent of CD14$^+$ cells, and proceeding with a type A or type B treatment if the tissue does not contain greater than 10 percent of CD14$^+$ cells. The renal cell carcinoma can be clear cell renal cell carcinoma. The step (a) can comprise determining whether or not the tumor tissue contains greater than 10 percent of CD14$^+$ cells. The step (a) can comprise determining whether or not the peritumoral tissue contains greater than 10 percent of CD14$^+$ cells. The step (a) can comprise determining whether or not the tumor or peritumoral tissue contains greater than 15 percent of CD14$^+$ cells. The step (a) can comprise determining whether or not the tumor or peritumoral tissue contains greater than 20 percent of CD14$^+$ cells. The step (a) can comprise determining whether or not the tumor or peritumoral tissue contains greater than 10 percent of CD14$^+$ cells in a diffuse staining pattern. The tumor or peritumoral tissue from the human can contain greater than 10 percent of CD14$^+$ cells. The method can comprise proceeding with a type B treatment selected from the group consisting of chemotherapies, biologic therapies, and cell therapies. The method can comprise proceeding with a type B treatment selected from the group consisting of treatment with Sunitinib, treatment with Sorafenib, treatment with Bevacizumab, treatment with Temsirolimus, and treatment with Everolimus. The method can comprise initiating a type B treatment for the human after the step (a). The tumor or peritumoral tissue from the human can lack greater than 10 percent of CD14$^+$ cells. The method can comprise performing a surgical treatment after the step (a).

In another aspect, this document features a method for treating a human having glioblastoma multiforme. The method comprises, or consists essentially of, (a) determining whether or not tumor or peritumoral tissue from the human contains greater than 10 percent of CD14$^+$ cells, and (b) proceeding with a conventional glioblastoma multiforme therapy if the tissue does not contain greater than 10 percent of CD14$^+$ cells, and proceeding with a therapy more aggressive than the conventional glioblastoma multiforme therapy if the tissue contains greater than 10 percent of CD14$^+$ cells. The conventional glioblastoma multiforme therapy can include temozolomide chemotherapy. The conventional glioblastoma multiforme therapy can include temozolomide chemotherapy after surgery. The conventional glioblastoma multiforme therapy can include temozolomide chemotherapy after radiotherapy. The conventional glioblastoma multiforme therapy can include temozolomide chemotherapy after surgery and radiotherapy. The therapy more aggressive than the conventional glioblastoma multiforme therapy can be an experimental therapy.

In another aspect, this document features a method for identifying a potential treatment agent for reducing cancer aggressiveness. The method comprises, or consists essentially of, (a) administering a test agent to a mammal having cancer, wherein a tumor or peritumoral tissue of the cancer contains a detectable level of CD14$^+$ cells, and (b) determining whether or not the level of CD14$^+$ cells present in the tumor or peritumoral tissue of the cancer is reduced as compared to the level of CD14$^+$ cells present in the tumor or peritumoral tissue of the cancer prior to the administering step (a), wherein a reduction in the level of CD14$^+$ cells present in the tumor or peritumoral tissue of the cancer indicates that the test agent is the potential treatment agent for reducing cancer aggressiveness. The mammal can be a human. The test agent can be a small molecule compound. The cancer can be a renal cell carcinoma. The cancer can be a clear cell renal cell carcinoma. The step (b) can comprise determining whether or not the level of CD14$^+$ cells present in a tumor tissue biopsy of the cancer obtained from the mammal after the administering step (a) is reduced. The step (b) can comprise determining whether or not the level of CD14$^+$ cells present in a peritumoral tissue biopsy of the cancer obtained from the mammal after the administering step (a) is reduced.

In another aspect, this document features a method for treating a human having a solid tumor. The method comprises, or consists essentially of, (a) determining whether or not tumor or peritumoral tissue from the human contains greater than 30 percent of CD14$^+$ cells, and (b) proceeding with a conventional ovarian cancer therapy if the tissue does not contain greater than 10 percent of CD14$^+$ cells, and proceeding with a therapy more aggressive than the conventional ovarian cancer therapy if the tissue contains greater than 10 percent of CD14$^+$ cells. The solid tumor can be a renal cell carcinoma.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to treating solid tumors (e.g., renal cell carcinomas and ovarian cancers). For example, this document provides methods and materials for assessing a renal cell carcinoma patient for tumor or peritumoral tissue containing CD14+ cells and proceeding with a renal cell carcinoma treatment option based on the presence, absence, or level of CD14+ cells present within the tumor or peritumoral tissue.

Figure 1:
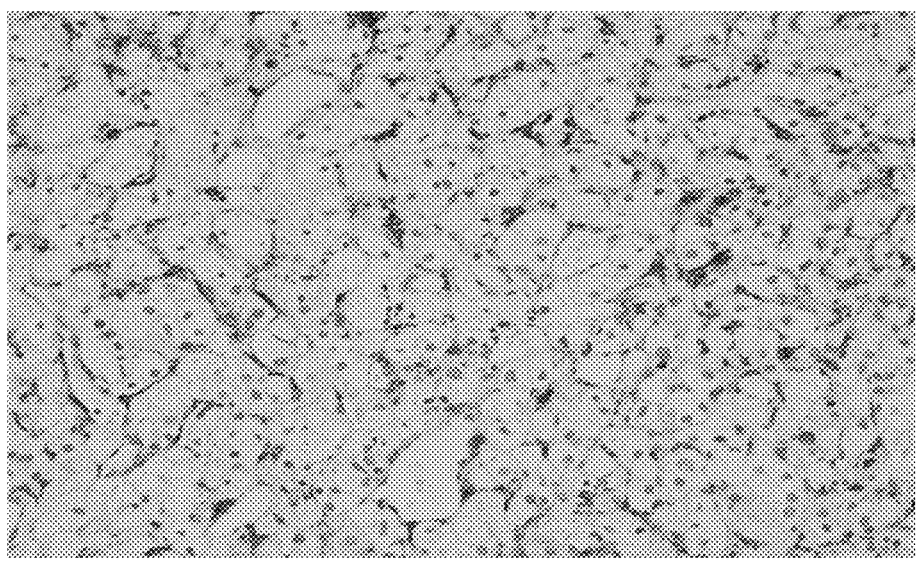
FIG. 1 is a photograph of an example of renal cell tumor tissue stained for CD14 expression demonstrating low or absent CD14 staining. Renal cell carcinoma tissue was obtained from a renal cell carcinoma patient having a low SSIGN score (e.g., SSIGN score of 2 or less) and stained with an anti-CD14 antibody.
Figure 2:
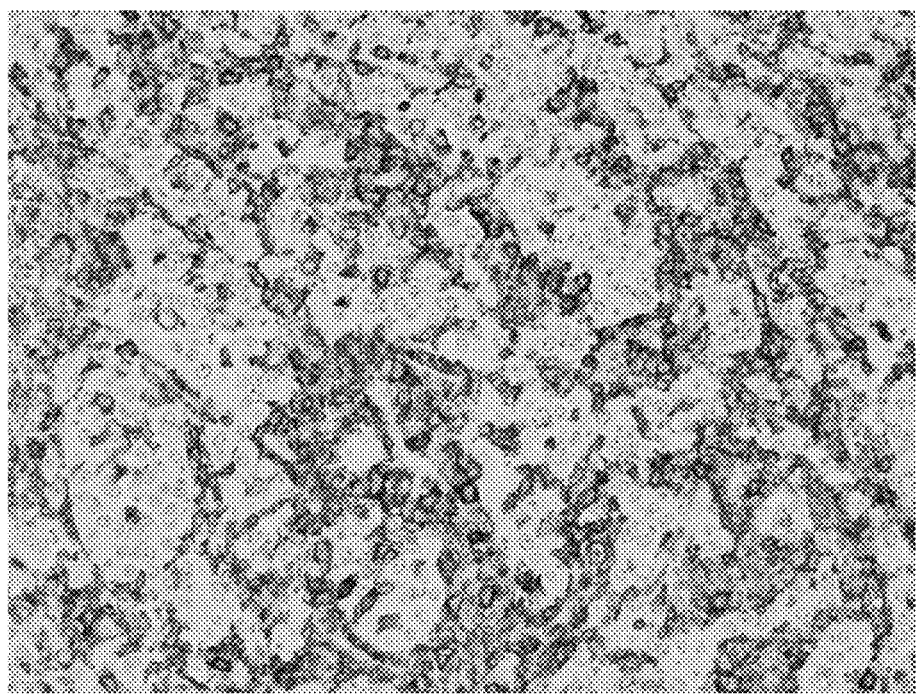
FIG. 2 is a photograph an example of renal cell carcinoma tissue stained for CD14 expression demonstrating high CD14 staining. Renal cell carcinoma tissue was obtained from a renal cell carcinoma patient having a high SSIGN score (e.g., SSIGN score of 7 or more) and stained with an anti-CD14 antibody.

As described herein, the presence of a moderate to marked level of CD14+ cells within tumor or peritumoral tissue of a renal cell carcinoma patient can indicate that it is unlikely that the renal cell carcinoma patient will respond positively to a type A treatment and that the renal cell carcinoma patient should proceed with a type B treatment. In general, a moderate level of CD14+ cells within tumor tissue or peritumoral tissue is a level where between about 10 and about 30 percent of the cells are CD14+ cells, while a marked level of CD14+ cells within tumor tissue or peritumoral tissue is a level where greater than about 30 percent of the cells are CD14+ cells. Typically, a tumor biopsy sample is obtained from a cancer patient using standard biopsy techniques. The tumor biopsy sample can include tumor tissue, peritumoral tissue, or both tumor tissue and peritumoral tissue. Once obtained, the sample can be treated such that the level of CD14+ cells present can be determined. Standard cell staining and immunoflourescence techniques can be used to determine the presence or absence of a moderate level or marked level of CD14+ cells within tissue. For example, a standard microscope can be used in connection with immunohistochemical staining techniques to determine the presence or absence of a moderate level or marked level of CD14+ cells within tissue (FIGS. 1 and 2). In some cases, CD14 expression within tumor tissue, peritumoral tissue, or both tumor tissue and peritumoral tissue can be assessed using a nucleic acid-based assay (e.g., reverse transcriptase-PCR or nucleic acid microarray assays). For example, CD14 expression levels within tumor tissue can be determined using a microarray having the ability to measure the amount of CD14 mRNA.

The presence of at least a moderate level of CD14+ cells within tumor or peritumoral tissue of a renal cell carcinoma patient can indicate that it is likely that the renal cell carcinoma patient will relapse quickly and should proceed with an experimental or non-standard treatment. In some cases, presence of at least a moderate level of CD14+ cells within tumor or peritumoral tissue of a renal cell carcinoma patient can indicate that it is unlikely that the renal cell carcinoma patient will respond positively to a type A treatment and that the renal cell carcinoma patient should proceed with a type B treatment. Examples of type A treatments can include, without limitation, surgery alone such as a partial nephrectomy, a simple nephrectomy, or a radical nephrectomy. Examples of type B treatments can include, without limitation, internal or external radiation therapies (e.g., x-ray or radioisotope therapy), chemotherapies, biologic therapies (e.g., immuno, antibody, or high dose IL-2 therapy), cell therapies (e.g., stem cell or vaccine therapy), treatment with Sunitinib (SU11248; an oral, small-molecule, multi-targeted receptor tyrosine kinase inhibitor), treatment with Sorafenib (BAY 43-9006, a small molecular inhibitor of several tyrosine protein kinases), treatment with Bevacizumab (a humanized monoclonal antibody that recognizes and blocks vascular endothelial growth factor), treatment with a rapamycin inhibitor (e.g., Temsirolimus (CCI-779) or Everolimus (RAD001)), and combinations thereof. In some cases, a type B treatment can be surgery (e.g., a partial nephrectomy, a simple nephrectomy, or a radical nephrectomy) in combination with one or more of the following therapies: an internal or external radiation therapy (e.g., x-ray or radioisotope therapy), chemotherapy, biologic therapy (e.g., immuno, antibody, or high dose IL-2 therapy), cell therapy (e.g., stem cell or vaccine therapy), treatment with Sunitinib, treatment with Sorafenib, treatment with Bevacizumab, and treatment with a rapamycin inhibitor (e.g., Temsirolimus (CCI-779) or Everolimus (RAD001)). In some cases, the absence of at least a moderate level of CD14+ cells within tumor or peritumoral tissue of a renal cell carcinoma patient (e.g., patients with low or absent CD14+ staining) can indicate that the patient should be observed but will likely experience a long period of tumor remission.

In some cases, the methods and materials provided herein can be used to treat glioblastoma multiforme (GBM) cancer. For example, the methods and materials provided herein can be used to assess a GBM patient for tumor or peritumoral tissue containing CD14+ cells. Once assessed, the patient can be instructed to proceed with a GBM treatment option based on the presence, absence, or level of CD14+ cells present within the GBM tumor or GBM peritumoral tissue. The presence of a moderate to marked level of CD14+ cells within tumor or peritumoral tissue of a GBM patient can indicate that it is unlikely that the GBM patient will respond positively to conventional (standard of care) therapy (e.g., temozolomide chemotherapy after surgery and radiotherapy) and should be included in an experimental or alternative therapy (e.g., immune based therapies including vaccine or antibody therapy, anti-angiogenesis therapies, cell based therapies, or experimental chemotherapies).

In some cases, the methods and materials provided herein can be used to treat ovarian cancer. For example, the methods and materials provided herein can be used to assess an ovarian cancer patient for tumor or peritumoral tissue containing CD14+ cells. Once assessed, the patient can be instructed to proceed with an ovarian cancer treatment option based on the presence, absence, or level of CD14+ cells present within the ovarian tumor or ovarian peritumoral tissue. The presence of a moderate to marked level of CD14+ cells within tumor or peritumoral tissue of an ovarian patient can indicate that it is unlikely that the ovarian patient will respond positively to conventional (standard of care) therapy and should be included in an experimental or alternative therapy.

This document also provides methods and materials for identifying treatment agents that are capable of reducing cancer aggressiveness (e.g., RCC aggressiveness). For example, patients having moderate to marked level of CD14+ cells within tumor or peritumoral tissue can be administered a potential treatment agent (e.g., small molecule compound). After administration of a potential treatment agent for a period of time (e.g., once a day to once a week for about two to three months), a tumor or peritumoral tissue biopsy can be obtained and assessed for a moderate to marked level of CD14+ cells. A reduction in the level of CD14+ cells within the tumor or peritumoral tissue as compared to the level determined prior to receiving the potential treatment agent can indicate that the potential treatment agent is an effective agent for reducing cancer aggressiveness.

The invention will be further described in the following examples, which do not limit the scope of the invention described in the claims.

EXAMPLES

Example 1

Intratumoral and Peritumoral CD14 Expression Among Patients with Clear Cell Renal Cell Carcinoma In a pilot study, ccRCC tumors with high Stage, Size, Grade, and Necrosis (SSIGN) scores were found to have significantly higher levels of CD14 expression compared with tumors with low SSIGN scores (Table 1). Briefly, CD14 expression was evaluated in 50 clear cell renal cell carcinoma (ccRCC) cases. The samples were randomly selected from a ccRCC cohort and consisted of 25 cases with low (0-2) and 25 cases with high (7+) SSIGN scores (Frank et al., *J. Urology*, 168:2395 (2002)). Intratumoral and peritumoral CD14 expression was quantitated as absent, focal, moderate, or marked.

TABLE 1

CD14 expression in 50 ccRCC cases.

| | SSIGN Score | | | |
|---|---|---|---|---|
| | Low | | High | |
| CD14 Expression | N = 25 | N (%) | N = 25 | P-value |
| Intratumoral | | | | |
| Absent | 2 (8) | | 1 (4) | 0.165 |
| Focal | 14 (56) | | 8 (32) | |
| Moderate | 7 (28) | | 9 (36) | |
| Marked | 2 (8) | | 7 (28) | |
| Intratumoral | | | | |
| Absent/Focal | 16 (64) | | 9 (36) | 0.048 |
| Moderate/Marked | 9 (36) | | 16 (64) | |
| Peritumoral (N = 46) | | | | |
| Absent | 2 (8) | | 0 | <0.001 |
| Focal | 19 (79) | | 6 (27) | |
| Moderate | 3 (13) | | 10 (46) | |
| Marked | 0 | | 6 (27) | |
| Peritumoral (N = 46) | | | | |
| Absent/Focal | 21 (87) | | 6 (27) | <0.001 |
| Moderate/Marked | 3 (13) | | 16 (73) | |
| Max of Intratumoral and Peritumoral | | | | |
| Absent | 1 (4) | | 0 | 0.017 |
| Focal | 13 (52) | | 5 (20) | |
| Moderate | 9 (36) | | 11 (44) | |
| Marked | 2 (8) | | 9 (36) | |
| Max of Intratumoral and Peritumoral | | | | |
| Absent/Focal | 14 (56) | | 5 (20) | 0.009 |
| Moderate/Marked | 11 (44) | | 20 (80) | |

In another study, the associations of tumor CD14 expression with clinical and pathologic features and patient outcome were determined using a large cohort of ccRCC patients.

Patient Selection

Using the Mayo Clinic Nephrectomy Registry, 375 patients treated with radical or partial nephrectomy for unilateral, sporadic, non-cystic ccRCC were identified.

Clinical and Pathologic Features

The clinical features studied included age, gender, and symptoms at presentation. Patients with a palpable flank or abdominal mass, discomfort, gross hematuria, acute onset varicocele, or the constitutional symptoms of rash, sweats, weight loss, fatigue, early satiety, or anorexia were considered symptomatic at presentation. The pathologic features studied included histologic subtype classified according to the Union Internationale Contre le Cancer, American Joint Committee on Cancer, and Heidelberg guidelines, the 2002 primary tumor classification, regional lymph node involvement, distant metastases, the 2002 TNM stage groupings, tumor size, nuclear grade, coagulative tumor necrosis, sarcomatoid differentiation, and SSIGN score. The SSIGN score is a composite scoring system developed specifically for patients with ccRCC based on primary tumor classification, regional lymph node involvement, distant metastases, tumor size, nuclear grade, and coagulative tumor necrosis. To obtain these features, a pathologist reviewed the microscope slides from all specimens without knowledge of patient outcome.

Patient Outcome

Vital status for patients in the Nephrectomy Registry is updated each year. If a patient died in the previous year, a death certificate was ordered to determine the cause of death. A visit to the institution within six months of the date of death for metastatic RCC was good documentation that RCC was the cause of death. If the death certificate does not support this, the medical history was reviewed by a urologist to determine the cause of death. If a death certificate cannot be obtained, the cause of death was verified with the patient's family or local physician.

Immunohistochemical Staining and Quantitation of CD14 Expression

A formalin-fixed, paraffin-embedded block with representative tumor tissue was selected for each patient in the cohort. Staining for CD14 was conducted as follows. Tissue sections were deparaffinized in xylene and rehydrated in a graded series of ethanols. Antigen-retrieval was performed by heating tissue sections in Target Retrieval solution pH 6 (Dako #S1699) to 121° C. using a Digital Decloaking Chamber (Biocare Medical, Walnut Creek, Calif.). Sections were cooled to 90° C. and incubated for an additional five minutes before the Decloaking Chamber was opened. Sections were washed in running $DH_2O$ for five minutes and incubated for five minutes in Wash Buffer (Dako #S3006) before being placed on the Autostainer Plus (Dako) for the following protocol. Sections were blocked for endogenous peroxidase for five minutes using Endogenous Blocking solution (Dako #S2001), washed twice in wash buffer, incubated five minutes in Background Reducer Sniper (Biocare Medical #BS966L), washed twice in wash buffer, and incubated for 60 minutes in purified rabbit anti-human CD14 antibody (Sigma PA #HPA001882) diluted 1:300 with DaVinci Green antibody diluent (Biocare Medical #PD900M). Sections were washed twice in wash buffer, incubated 15 minutes in the rabbit probe from the Mach 3 Rabbit HRP-Polymer Kit (Biocare Medical #M3R531L), washed twice in wash buffer, and incubated 15 minutes with the rabbit polymer from the Rabbit HRP-Polymer Kit. Sections were washed with wash buffer and visualized by incubating Betazoid DAB (Biocare Medical #BDB2004L) for eight minutes. Sections were washed with $DH_2O$, counterstained with hematoxylin, dehydrated in ethanol, and cleared in xylene. Coverslips were mounted in permanent mounting media. All stained slides were reviewed and quantitated by a pathologist without knowledge of patient outcome. Intratumoral and (if possible) peritumoral CD14 expression was assessed as absent, focal, moderate, or marked.

Statistical Methods

Associations of CD14 expression with clinical and pathologic features were evaluated using chi-square tests. Associations of CD14 expression with cancer-specific survival were illustrated using Kaplan-Meier curves. The magnitudes of the associations of CD14 expression with death from RCC were evaluated using Cox proportional hazards regression models and summarized with hazard ratios (HRs) and 95% confidence intervals (CI). The duration of follow-up was calculated from the date of nephrectomy to the date of death or last follow-up. Patients who died from causes other than RCC were censored at the date of death, while patients who were still alive at the time of analysis were censored at the date of last follow-up. Statistical analyses were performed using the SAS software package (SAS Institute; Cary, N.C.). All tests were two-sided, and p-values <0.05 were considered statistically significant.

Results

Clinical and Pathologic Features

A summary of clinical and pathologic features for the 375 ccRCC patients studied is provided in Table 2. Mean age at surgery was 63 years (median 63; range 26-87); mean tumor size was 6.8 cm (median 5.8; range 1.0-22.0); and mean SSIGN Score was 3.9 (median 3; range 0-15).

TABLE 2

Clinical and pathologic features for 375 ccRCC patients.

| Feature | N (%) |
|---|---|
| Age at surgery (years) | |
| <65 | 204 (54.4) |
| ≥65 | 171 (45.6) |
| Gender | |
| Female | 113 (30.1) |
| Male | 262 (69.9) |
| Symptoms | 192 (51.2) |
| Constitutional symptoms | 50 (13.3) |
| 2002 Primary tumor classification | |
| pT1a | 114 (30.4) |
| pT1b | 94 (25.1) |
| pT2 | 71 (18.9) |
| pT3a | 40 (10.7) |
| pT3b | 50 (13.3) |
| pT3c | 3 (0.8) |
| pT4 | 3 (0.8) |
| Regional lymph node involvement | |
| pNX and pN0 | 349 (93.1) |
| pN1 and pN2 | 26 (6.9) |
| Distant metastases | |
| M0 | 324 (86.4) |
| M1 | 51 (13.6) |
| 2002 TNM stage groupings | |
| I | 203 (54.1) |
| II | 54 (14.4) |
| III | 62 (16.5) |
| IV | 56 (14.9) |

TABLE 2-continued

Clinical and pathologic features for 375 ccRCC patients.

| Feature | N (%) |
|---|---|
| Tumor size (cm) | |
| <5 | 144 (38.4) |
| 5 to <7 | 73 (19.5) |
| 7 to <10 | 75 (20.0) |
| ≥10 | 83 (22.1) |
| Nuclear grade | |
| 1 | 24 (6.4) |
| 2 | 136 (36.3) |
| 3 | 183 (48.8) |
| 4 | 32 (8.5) |
| Coagulative tumor necrosis | 97 (25.9) |
| Sarcomatoid differentiation | 17 (4.5) |
| SSIGN score | |
| Low (0-2) | 175 (46.7) |
| Intermediate (3-6) | 111 (29.6) |
| High (≥7) | 89 (23.7) |

CD14 Expression

Intratumoral, peritumoral, and maximal CD14 expression between the two are summarized in Table 3. A comparison of intratumoral and peritumoral expression is provided in Table 4. Associations of maximal CD14 expression with clinical and pathologic features are summarized in Table 5. Since only six tumors did not demonstrate intratumoral or peritumoral CD14 expression, these tumors were combined with those with focal expression for analysis. CD14 expression, particularly marked CD14 expression, was significantly associated with symptoms at presentation, larger tumors of later stage and higher grade, coagulative tumor necrosis, sarcomatoid differentiation, and higher SSIGN scores. For example, median SSIGN scores for tumors with absent/focal, moderate, and marked CD14 expression were 1, 5, and 7, respectively.

TABLE 3

CD14 expression for 375 ccRCC patients.

| CD14 Expression | N (%) |
|---|---|
| Intratumoral | |
| Absent | 11 (2.9) |
| Focal | 224 (59.7) |
| Moderate | 100 (26.7) |
| Marked | 40 (10.7) |
| Peritumoral (N = 373) | |
| Absent | 9 (2.4) |
| Focal | 204 (54.7) |
| Moderate | 133 (35.7) |
| Marked | 27 (7.2) |
| Maximal Intratumoral and Peritumoral | |
| Absent | 6 (1.6) |
| Focal | 178 (47.5) |
| Moderate | 142 (37.9) |
| Marked | 49 (13.1) |

TABLE 4

CD14 expression for 375 ccRCC patients.

| Intratumoral | Peritumoral | | | | |
|---|---|---|---|---|---|
| | Missing | Absent | Focal | Moderate | Marked |
| Absent | 0 | 6 | 5 | 0 | 0 |
| Focal | 0 | 3 | 170 | 51 | 0 |
| Moderate | 1 | 0 | 27 | 63 | 9 |
| Marked | 1 | 0 | 2 | 19 | 18 |

TABLE 5

Associations of CD14 expression with clinical and pathologic features for 375 ccRCC patients.

| | Maximal Intratumoral and Peritumoral CD14 | | | |
|---|---|---|---|---|
| Feature | Absent/Focal N = 184 | Moderate N = 142 N (%) | Marked N = 49 | P-value |
| Age at surgery (years) | | | | |
| <65 | 109 (59.2) | 73 (51.4) | 22 (44.9) | 0.133 |
| ≥65 | 75 (40.8) | 69 (48.6) | 27 (55.1) | |
| Gender | | | | |
| Female | 64 (34.8) | 35 (24.7) | 14 (28.6) | 0.137 |
| Male | 120 (65.2) | 107 (75.4) | 35 (71.4) | |
| Symptoms | 74 (40.2) | 88 (62.0) | 30 (61.2) | <0.001 |
| Constitutional symptoms | 13 (7.1) | 20 (14.1) | 17 (34.7) | <0.001 |
| 2002 Primary tumor classification | | | | |
| pT1a and pT1b | 138 (75.0) | 60 (42.3) | 10 (20.4) | <0.001 |
| PT2 | 27 (14.7) | 30 (21.1) | 14 (28.6) | |
| pT3a, pT3b, pT3c, and pT4 | 19 (10.3) | 52 (36.6) | 25 (51.0) | |
| Regional lymph node involvement | | | | |
| pNX and pN0 | 179 (97.3) | 128 (90.1) | 42 (85.7) | 0.004 |
| pN1 and pN2 | 5 (2.7) | 14 (9.9) | 7 (14.3) | |
| Distant metastases | | | | |
| M0 | 172 (93.5) | 118 (83.1) | 34 (69.4) | <0.001 |
| M1 | 12 (6.5) | 24 (16.9) | 15 (30.6) | |
| 2002 TNM stage groupings | | | | |
| I | 136 (73.9) | 58 (40.9) | 9 (18.4) | <0.001 |
| II | 25 (13.6) | 22 (15.5) | 7 (14.3) | |
| III | 10 (5.4) | 34 (23.9) | 18 (36.7) | |
| IV | 13 (7.1) | 28 (19.7) | 15 (30.6) | |
| Tumor size (cm) | | | | |
| <5 | 100 (54.4) | 37 (26.1) | 7 (14.3) | <0.001 |
| 5 to <7 | 35 (19.0) | 28 (19.7) | 10 (20.4) | |
| 7 to <10 | 31 (16.9) | 32 (22.5) | 12 (24.5) | |
| ≥10 | 18 (9.8) | 45 (31.7) | 20 (40.8) | |
| Nuclear grade | | | | |
| 1 | 17 (9.2) | 7 (4.9) | 0 | <0.001 |
| 2 | 99 (53.8) | 34 (23.9) | 3 (6.1) | |
| 3 | 66 (35.9) | 87 (61.3) | 30 (61.2) | |
| 4 | 2 (1.1) | 14 (9.9) | 16 (32.7) | |
| Coagulative tumor necrosis | 12 (6.5) | 53 (37.3) | 32 (65.3) | <0.001 |
| Sarcomatoid differentiation | 1 (0.5) | 7 (4.9) | 9 (18.4) | <0.001 |
| SSIGN score | | | | |
| Low (0-2) | 128 (69.6) | 44 (31.0) | 3 (6.1) | <0.001 |
| Intermediate (3-6) | 42 (22.8) | 53 (37.3) | 16 (32.7) | |
| High (≥7) | 14 (7.6) | 45 (31.7) | 30 (61.2) | |

Patient Outcome

At last follow-up, 159 patients had died, including 100 who died from RCC at a mean of 2.3 years following surgery (median 1.7; range 0-9). Among the 216 patients who were still alive at last follow-up, the mean duration of follow-up was 7.1 years (median 7.3; range 0-10); only 5 (2.3%) patients had fewer than 2 years of follow-up. Estimated cancer-specific survival rates (95% CI, number still at risk) at 1, 3, 5, and 7 years following surgery were 91.0% (88.1-94.0; 328), 79.0% (74.9-83.4; 268), 75.3% (70.9-80.0; 232), and 71.9% (67.3-77.0; 136), respectively.

Figure 3:
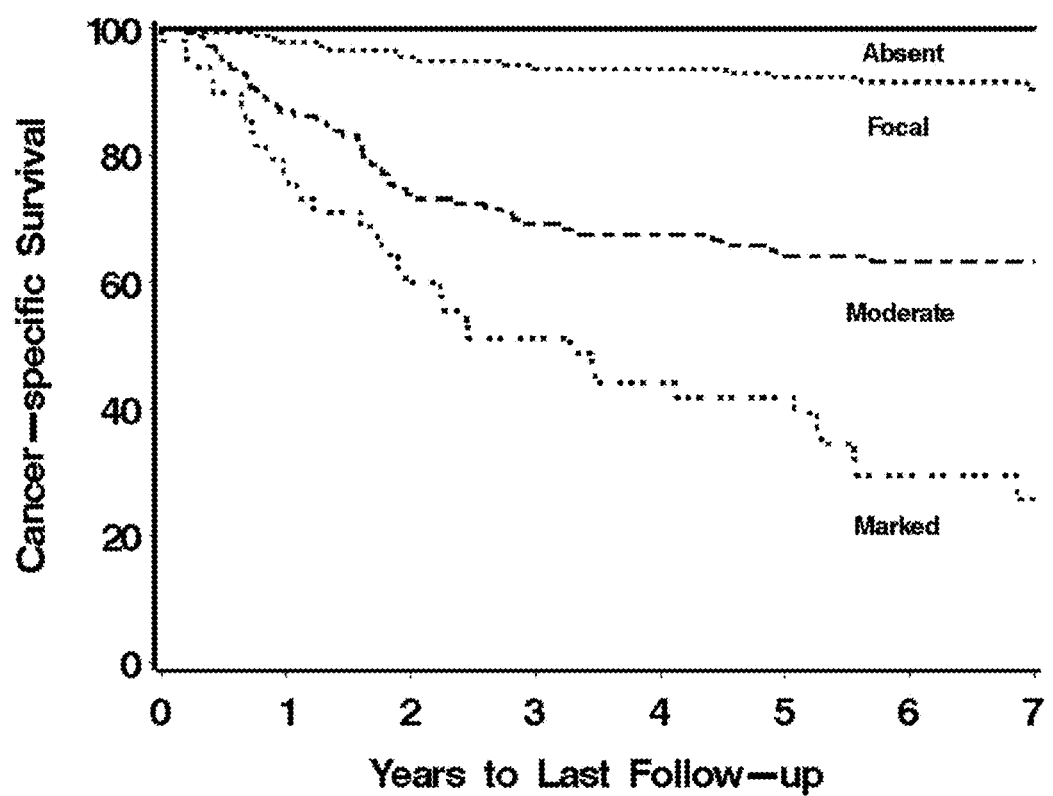
FIG. 3. Cancer-specific survival following surgery by maximal intratumoral and peritumoral CD14 expression for 375 ccRCC patients. Estimated cancer-specific survival rates (95% CI; number still at risk) at 5 years following surgery were 100% (100-100; 6), 92.2% (88.2-96.4; 134), 64.1% (56.4-73.0; 75), and 41.8% (29.6-58.9; 17) for patients with tumors with absent, focal, moderate, and marked CD14 expression, respectively.

The association of maximal intratumoral and peritumoral CD14 expression with cancer-specific survival was determined (FIG. 3). The magnitudes of the associations of CD14 expression with death from RCC are summarized in Table 6. Univariately, patients whose tumors contained moderate CD14 expression were nearly five times more likely to die from RCC compared with patients whose tumors contained absent/focal CD14 expression (HR 4.79; p<0.001). Patients whose tumors contained marked CD14 expression were over 11 times more likely to die from RCC compared with patients whose tumors contained absent/focal CD14 expression (HR 11.51; p<0.001). These associations were also evaluated in a multivariable setting adjusting for the SSIGN score. After accounting for the association between SSIGN score and death from RCC, the HRs for the associations of moderate and marked CD14 expression with death from RCC were 2.87 (p<0.001) and 3.03 (p<0.001), respectively. After further adjustment for age at surgery, gender, symptoms at presentation, sarcomatoid differentiation, and the SSIGN score, the HRs for the associations of moderate and marked CD14 expression with death from RCC were 2.53 (95% CI 1.45-4.42; p=0.001) and 2.69 (1.44-5.01; p=0.002), respectively.

TABLE 6

Univariate and multivariable associations of CD14 expression with death from RCC for 375 patients with ccRCC.

| CD14 Expression | HR (95% CI) | P-value |
|---|---|---|
| | Univariate | |
| Maximal Intratumoral and Peritumoral | | |
| Absent/Focal | 1.0 (reference) | |
| Moderate | 4.79 (2.76-8.32) | <0.001 |
| Marked | 11.51 (6.39-20.73) | <0.001 |
| | Adjusted for SSIGN Score | |
| Maximal Intratumoral and Peritumoral | | |
| Absent/Focal | 1.0 (reference) | |
| Moderate | 2.87 (1.65-5.00) | <0.001 |
| Marked | 3.03 (1.65-5.58) | <0.001 |

Example 2

Treating Renal Cell Carcinoma Patients

A newly diagnosed RCC patient who is currently not being treated and who has a high level of $CD14^+$ cells within tumor or peritumoral tissue is treated with standard of care (e.g., surgery), but is subjected to increased surveillance as this patient is highly likely to relapse and/or experience metastasis.

A newly diagnosed RCC patient who is currently not being treated and who has no $CD14^+$ cells within tumor or peritumoral tissue is treated by surgery if indicated and observation.

An RCC patient who is currently being treated with a standard cancer treatment and who has a high level of $CD14^+$ cells within tumor or peritumoral tissue is included in a clinical trial or other aggressive therapy without waiting for relapse.

An RCC patient who is currently being treated with a standard cancer treatment and who has no $CD14^+$ cells within tumor or peritumoral tissue is under a routine schedule of observation without additional treatment.

Example 3

Correlation Between Intratumoral $CD14^+$ Cell Levels and $CD14^+/DR^-$ Peripheral Blood Levels A group of 17 patients had tumor samples that were assessed for the level of CD14+ cells and had peripheral blood samples that were assessed for CD14 and HLA-DR staining. The tumor samples were classified as having a high intensity of $CD14^+$ staining (high), a medium intensity of $CD14^+$ staining (medium), or a low/no intensity of $CD14^+$ staining (low/none). The peripheral blood samples were assessed to determine the mean fluorescence intensity (MFI) of $HLA-DR^+$ staining for peripheral blood cells that are $CD14^+$.

Figure 4:
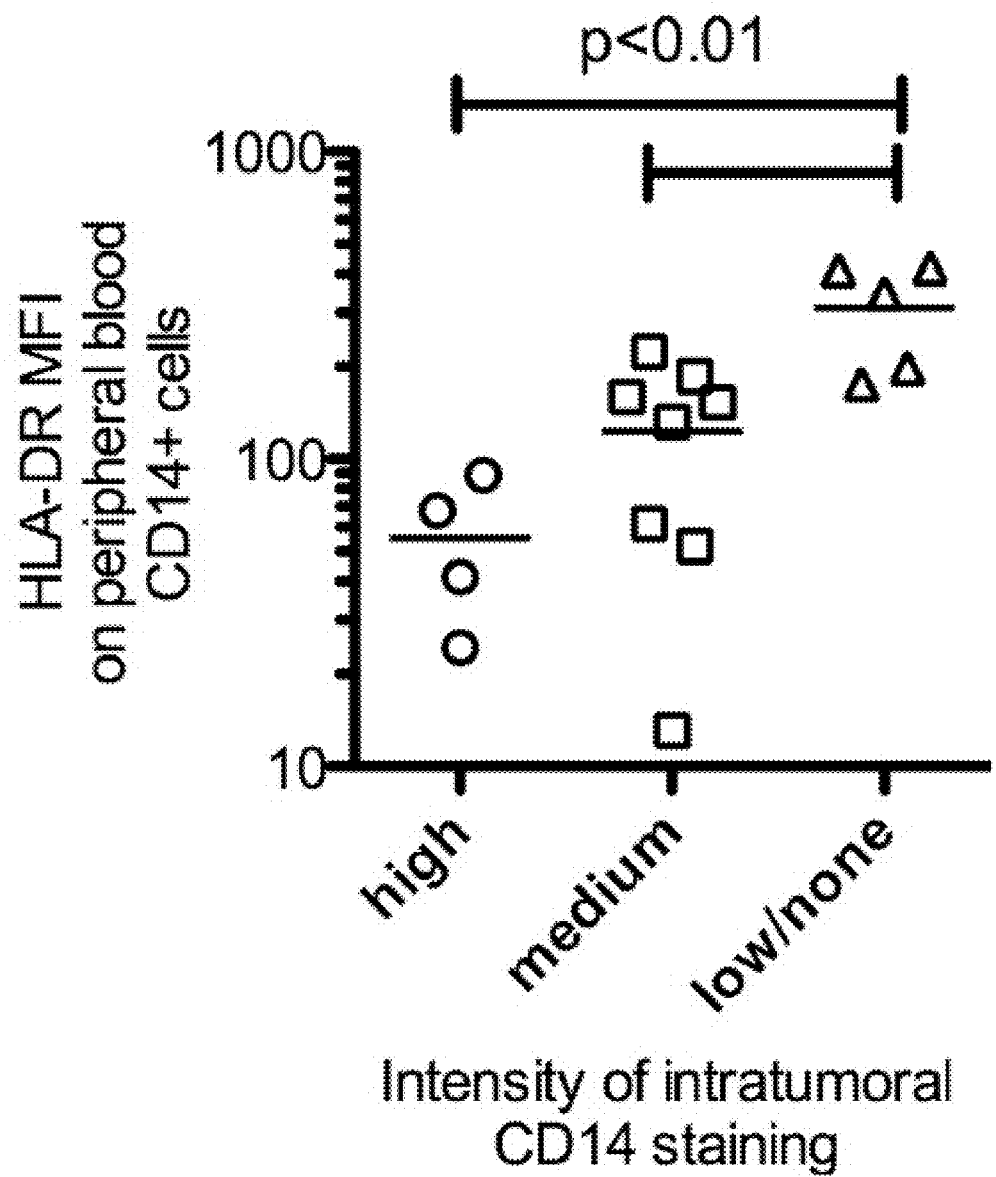
FIG. 4 is a graph plotting the HLA-DR mean fluorescence intensity (MFI) of peripheral blood cells that are CD14+ and obtained from patients having tumor tissue with a high intensity of CD14+ staining (high), a medium intensity of CD14+ staining (medium), or a low/no intensity of CD14+ staining (low/none).

As the level of $CD14^+$ staining increases in intratumoral tissue, more $CD14^+$ cells in the periphery lose HLA-DR expression (FIG. 4). These results demonstrate that there is an association between the level of intratumoral $CD14^+$ cells and the level of peripheral $CD14^+/DR^-$ cells. These results also demonstrate that the level of $CD14^+/DR^-$ cells can be used to measure the intratumoral level of $CD14^+$ cells, and therefore be an accurate surrogate for the tumor staining.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for treating a human having glioblastoma multiforme, wherein said method comprises:
   (a) determining that tumor or peritumoral tissue from said human having glioblastoma multiforme contains greater than 10 percent of $CD14^+$ cells, and
   (b) administering an immune-based therapy, an anti-angiogenesis therapy, or a cell-based therapy to said human having glioblastoma multiforme when it is determined that said tumor or peritumoral tissue contains greater than 10 percent of $CD14^+$ cells.

* * * * *